US005623131A

United States Patent [19]
Earnest

[11] Patent Number: 5,623,131
[45] Date of Patent: Apr. 22, 1997

[54] PROTECTIVE STETHOSCOPE COVER HAVING A HEAD COVER CONNECTED TO A BODY COVER

[76] Inventor: Tommy L. Earnest, 2465 Plum Creek Rd., Christiansburg, Va. 24073

[21] Appl. No.: 503,503

[22] Filed: Jul. 18, 1995

[51] Int. Cl.$^6$ .................................................. A61B 7/02
[52] U.S. Cl. .................. 181/131; 128/715; 128/DIG. 15; D24/134
[58] Field of Search ............................ 128/715, DIG. 15; D24/134; 181/131

[56] References Cited

U.S. PATENT DOCUMENTS

| | | | |
|---|---|---|---|
| D. 303,146 | 8/1989 | Stamm | D24/20 |
| D. 344,798 | 3/1994 | Baskin | D24/134 |
| 3,867,925 | 2/1975 | Ersek | 128/715 |
| 5,082,111 | 1/1992 | Corbitt, Jr. et al. | 128/DIG. 15 |
| 5,172,683 | 12/1992 | West | D24/134 |
| 5,269,314 | 12/1993 | Kendall et al. | 128/715 |
| 5,365,023 | 11/1994 | Lawton | 128/715 |
| 5,428,193 | 6/1995 | Mandiberg | 128/715 |
| 5,466,898 | 11/1995 | Gilbert et al. | 181/131 |
| 5,486,659 | 1/1996 | Rosenbush | 181/131 |
| 5,539,162 | 7/1996 | Tuttle | 181/131 |
| 5,564,431 | 10/1996 | Seward | 128/715 |

*Primary Examiner*—William E. Kamm
*Assistant Examiner*—Carl H. Layno

[57] ABSTRACT

A cover encloses the center sound tube and head of a stethoscope. The head cover can be extended over the head of a stethoscope and may be separate from or coupled to the center sound tube cover. A cover flap can extend over an upper end of the center sound tube cover and between lateral sound tubes of the stethoscope to preclude an unintentional engagement with hair.

3 Claims, 4 Drawing Sheets

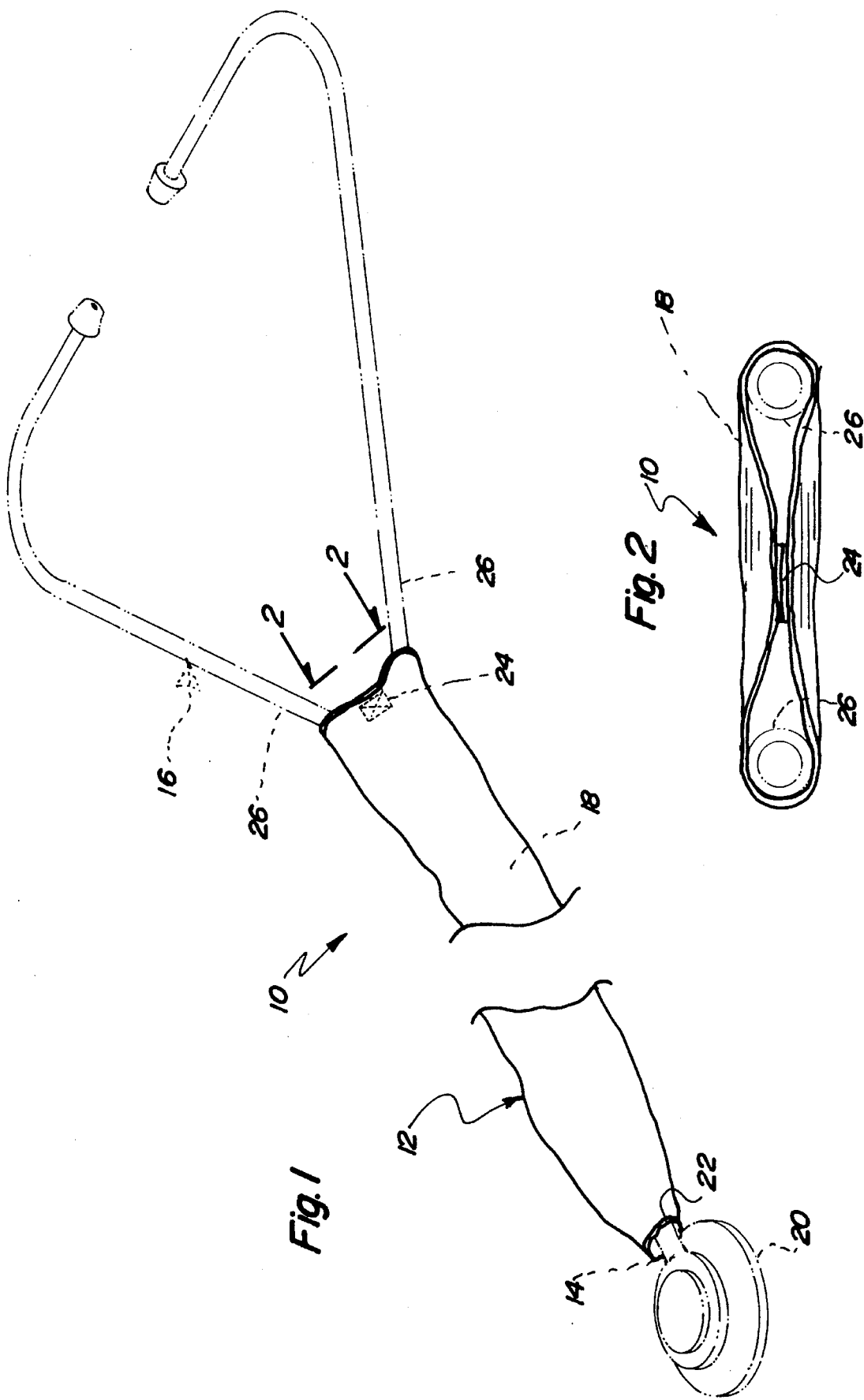

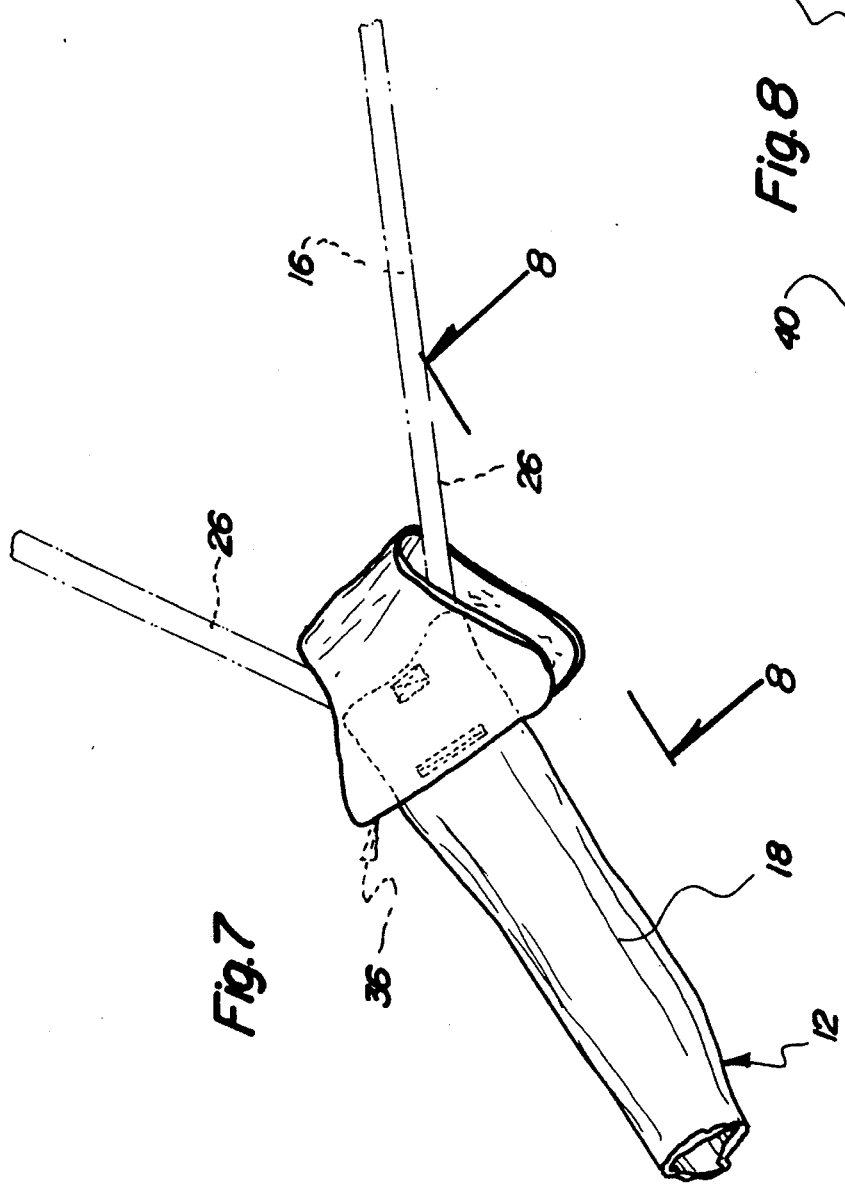
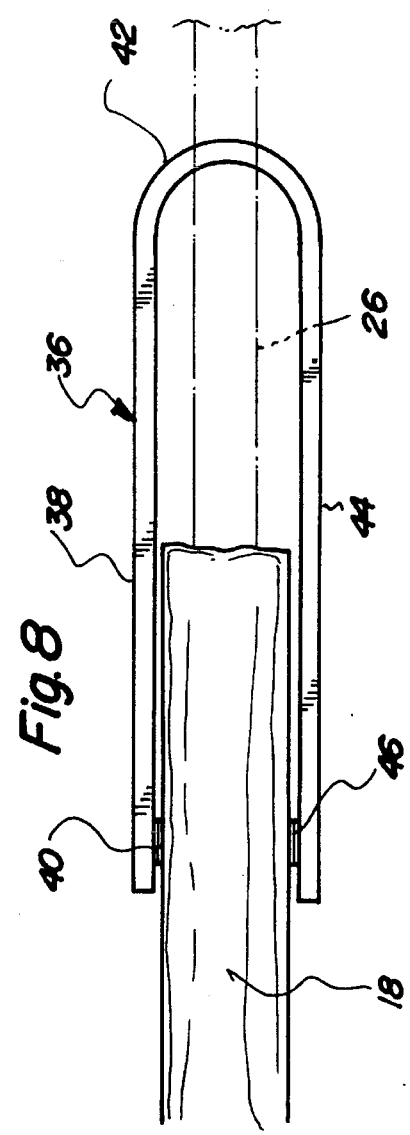

PROTECTIVE STETHOSCOPE COVER HAVING A HEAD COVER CONNECTED TO A BODY COVER

BACKGROUND OF THE INVENTION

1. Field of the Invention

The present invention relates to medical device coverings and more particularly pertains to a protective stethoscope cover for enclosing portions of a stethoscope.

2. Description of the Prior Art

The use of medical device coverings is known in the prior art. More specifically, medical device coverings heretofore devised and utilized are known to consist basically of familiar, expected and obvious structural configurations, notwithstanding the myriad of designs encompassed by the crowded prior art which have been developed for the fulfillment of countless objectives and requirements.

Known prior art medical device coverings include U.S. Pat. No. 5,269,314; U.S. Pat. No. 4,867,265; U.S. Pat. No. 4,461,368; U.S. Pat. No. 4,871,046; U.S. Design Pat. No. 349,959; and U.S. Design Pat. No. 344,798.

While these devices fulfill their respective, particular objectives and requirements, the aforementioned patents do not disclose a protective stethoscope cover for enclosing portions of a stethoscope which includes a center sound tube cover receiving a center sound tube of a stethoscope, a head cover positionable over a head of the stethoscope, and a cover flap extending over an upper end of the center sound tube cover and between lateral sound tubes of the stethoscope to preclude unintentional engagement with hair.

In these respects, the protective stethoscope cover according to the present invention substantially departs from the conventional concepts and designs of the prior art, and in so doing provides an apparatus primarily developed for the purpose of enclosing portions of a stethoscope.

SUMMARY OF THE INVENTION

In view of the foregoing disadvantages inherent in the known types of medical device coverings now present in the prior art, the present invention provides a new protective stethoscope cover construction wherein the same can be utilized for enclosing portions of a stethoscope. As such, the general purpose of the present invention, which will be described subsequently in greater detail, is to provide a new protective stethoscope cover apparatus and method which has many of the advantages of the medical device coverings mentioned heretofore and many novel features that result in a protective stethoscope cover which is not anticipated, rendered obvious, suggested, or even implied by any of the prior art medical device coverings, either alone or in any combination thereof.

To attain this, the present invention generally comprises cover for enclosing portions of a stethoscope. The inventive device includes a center sound tube cover receiving a center sound tube of a stethoscope. A head cover can be extended over a head of the stethoscope and may be separate from or coupled to the center sound tube cover. A cover flap can extend over an upper end of the center sound tube cover and between lateral sound tubes of the stethoscope to preclude an unintentional engagement with hair.

There has thus been outlined, rather broadly, the more important features of the invention in order that the detailed description thereof that follows may be better understood, and in order that the present contribution to the art may be better appreciated. There am additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new protective stethoscope cover apparatus and method which has many of the advantages of the medical device coverings mentioned heretofore and many novel features that result in a protective stethoscope cover which is not anticipated, rendered obvious, suggested, or even implied by any of the prior art tool guides, either alone or in any combination thereof.

It is another object of the present invention to provide a new protective stethoscope cover which may be easily and efficiently manufactured and marketed.

It is a further object of the present invention to provide a new protective stethoscope cover which is of a durable and reliable construction.

An even further object of the present invention is to provide a new protective stethoscope cover which is susceptible of a low cost of manufacture with regard to both materials and labor, and which accordingly is then susceptible of low prices of sale to the consuming public, thereby making such protective stethoscope covers economically available to the buying public.

Still yet another object of the present invention is to provide a new protective stethoscope cover which provides in the apparatuses and methods of the prior art some of the advantages thereof, while simultaneously overcoming some of the disadvantages normally associated therewith.

Still another object of the present invention is to provide a new protective stethoscope cover for enclosing portions of a stethoscope.

Yet another object of the present invention is to provide a new protective stethoscope cover which includes a center sound tube cover receiving a center sound tube of a stethoscope, a head cover positionable over a head of the stethoscope, and a cover flap extending over an upper end of the center sound tube cover and between lateral sound tubes of the stethoscope to preclude unintentional engagement with hair.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of a protective stethoscope cover according to the present invention in use.

FIG. 2 is an elevation view taken from line 2—2 of FIG. 1.

FIG. 7 is an isometric illustration of the invention including a cover flap.

FIG. 8 is an elevation view taken from line 8—8 of FIG. 7.

DESCRIPTION OF THE PREFERRED EMBODIMENT

Figure 3:
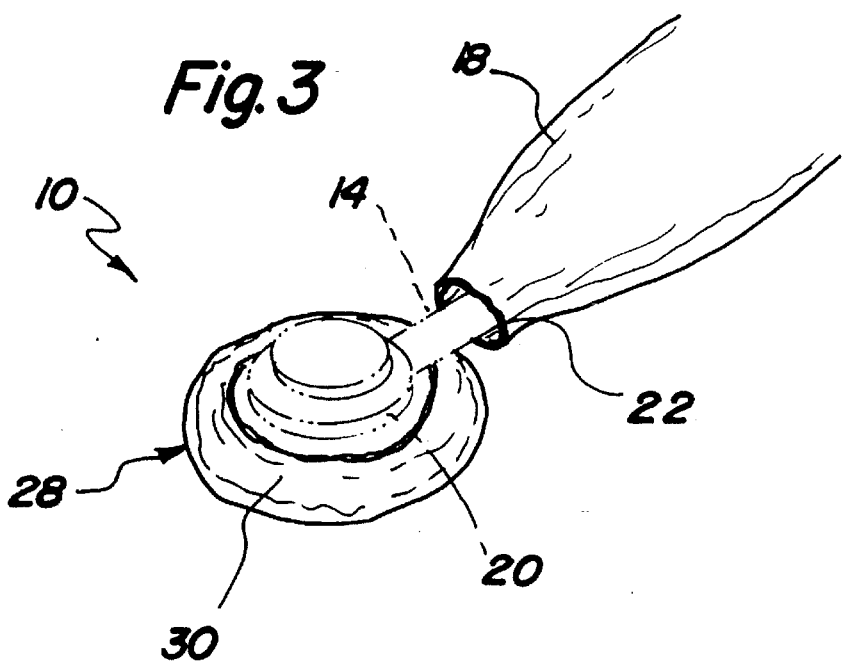
FIG. 3 is an isometric illustration of the invention including a head cover.

With reference now to the drawings, and in particular to FIGS. 1–8 thereof, a new protective stethoscope cover embodying the principles and concepts of the present invention and generally designated by the reference numeral 10 will be described.

More specifically, it will be noted that the protective stethoscope cover 10 comprises a center sound tube cover 12 for receiving and at least partially enclosing a center sound tube 14 of a stethoscope 16 such as is shown in FIG. 1 of the drawings. By this structure, contact of the center sound tube 14 against skin of a user or other surrounding object is substantially reduced.

As best illustrated in FIGS. 1 and 2, it can be shown that the sound tube cover 12 of the present invention 10 preferably comprises an elongated flexible sheath 18 having a transverse dimension sufficient to receive a head 20 of the stethoscope 16 therethrough during installation of the device 10 relative to a stethoscope. The flexible sheath 18 is provided at a first end thereof with an elastic collar 22 positionable proximal to a juncture of the center sound tube 14 of the stethoscope 16 with the head 20 thereof. A second end of the flexible sheath 18 is provided with a hook and loop closure 24 which operates to couple diametrically opposed interior portions of the flexible sheath 18 together to permit projection of lateral sound tubes 26 of the stethoscope 16 from opposed sides of the hook and loop closure 24, such as is indicated in FIG. 2 of the drawings. The flexible sheath 18 may be comprised of any substantially flexible material, and is preferably comprised of a flexible polymeric material which may be disposable and biodegradable.

Figure 4:
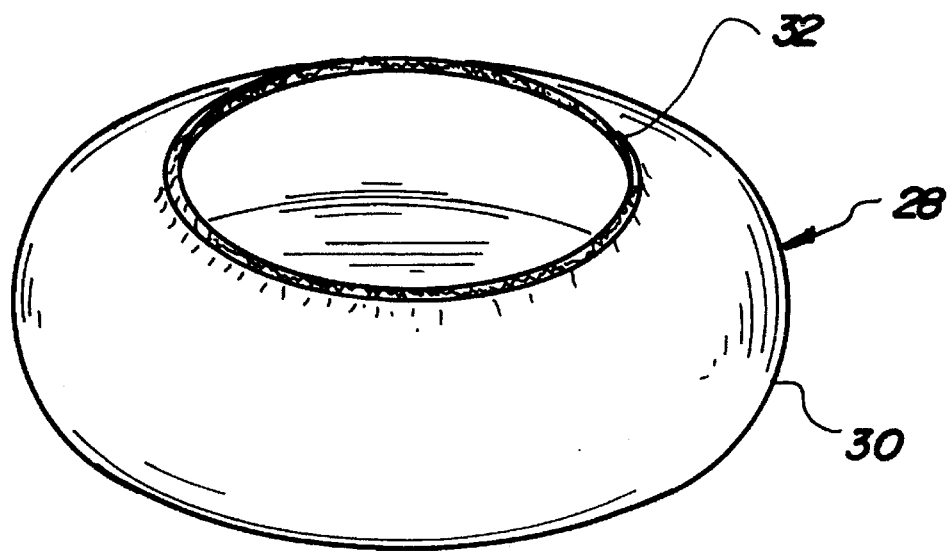
FIG. 4 is an isometric illustration of the head cover, per se.
Figure 5:
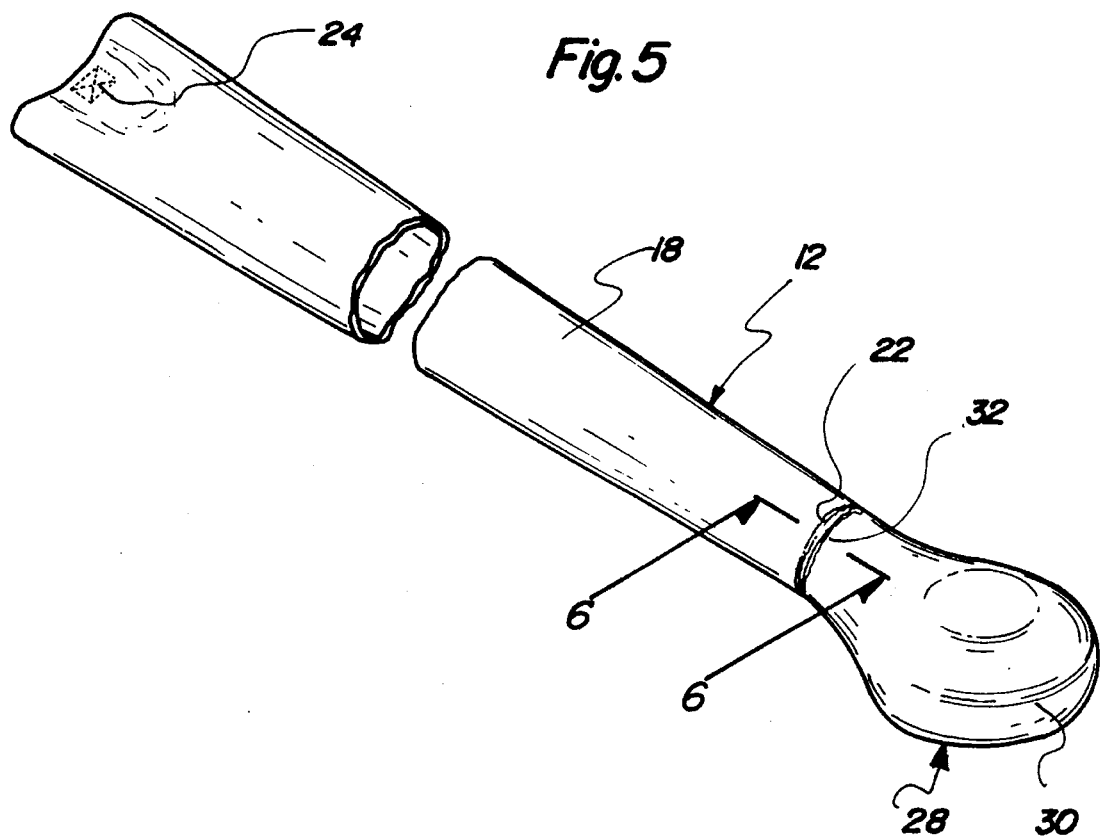
FIG. 5 is an isometric illustration of an alternative form of the invention.
Figure 6:
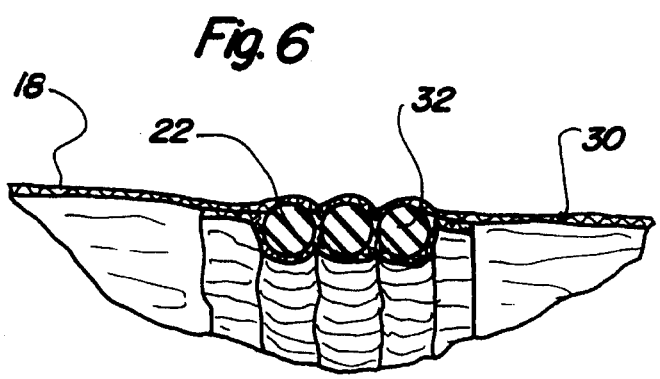
FIG. 6 is a cross sectional view taken along line 6—6 of FIG. 5.

Referring now to FIGS. 3 and 4, it can be shown that the present invention 10 may further comprise a head cover 28 securable to the head 20 of the stethoscope 16. To this end, and as best illustrated in FIG. 4, the head cover 28 comprises a semi-spherical cover 30 having an elastic neck opening 32 permitting insertion of the head 20 thereinto. The semi-spherical cover 30 may also be comprised of a disposable polymeric material similar to that of the flexible sheath 18 as described above. As shown in FIGS. 5 and 6, an alternative form of the present invention 10 may comprise coupling of the elastic neck opening 32 of the semi-spherical cover 30 to the elastic collar 22 of the flexible sheath 18. By this structure, both the head 20 and the center sound tube 14 can be fully enclosed within the present invention 10.

Referring to FIGS. 7 and 8, it can be shown that the present invention 10 may further comprise a cover flap 36 removably coupled to diametrically opposed exterior surfaces of the second end of the flexible sheath 18 of the center sound tube 12. To this end, and as shown in FIG. 8, the cover flap 36 preferably comprises an upper web 38 removably secured to an upper exterior portion of the flexible sheath 18 by a first pair of hook and loop patches 40 interposed therebetween. The upper web 38 continues into a connecting web 42 extendable between the lateral sound tubes 26 of the stethoscope 16 and folds back into a parallel orientation with the upper web 38 to terminate in a lower web 44. The lower web 44 is of substantially coextensive construction relative to the upper web 38 and is similarly removably coupled to a lower exterior surface of the flexible sheath 18 in a diametrically opposed orientation relative to the coupling of the upper web 38 to the flexible sheath by a second pair of hook and loop patches 46 interposed between the lower web 44 and the flexible sheath 18. By this structure, the second end of the flexible sheath 18 is protected from ingress of objects such as human hair or the like thereinto which could engage portions of the present invention 10 of the stethoscope 16 in an undesirable manner.

In use, the protective stethoscope cover 10 according to the present invention can be easily utilized for enclosing various portions of a stethoscope 16 as described above. The present invention 10 thus serves to eliminate irritation of the stethoscope tubing a result of contact therewith against skin or like tissues, and further serves to extend a useful life of portions of the stethoscope 16 by protecting the same from contact with damaging fluids or heat such as body oil and body heat.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A protective stethoscope cover comprising:

a center sound tube cover for receiving and at least partially enclosing a center sound tube of a stethoscope;

wherein the sound tube cover comprises an elongated flexible sheath having a transverse dimension sufficient to receive a head of a stethoscope therethrough;

wherein the sound tube cover further comprises an elastic collar secured to the flexible sheath at a first end thereof; wherein the sound tube cover further comprises a hook and loop closure secured to a second end of the flexible sheath, the hook and loop closure being adapted to couple diametrically opposed interior portions of the flexible sheath together to permit projection of lateral sound tubes of a stethoscope from opposed sides of the hook and loop closure;

a head cover securable to a head of a stethoscope, the head cover comprises a semi-spherical cover having an elastic neck opening permitting insertion of the head thereinto, wherein the elastic neck opening of the semi-spherical cover is sealingly coupled to the elastic collar of the flexible sheath.

2. The protective stethoscope cover of claim 1, further comprising a cover flap removably coupled to diametrically opposed exterior surfaces of the second end of the flexible sheath of the center sound tube of a stethoscope.

3. The protective stethoscope cover of claim 2, wherein the cover flap comprises an upper web removably secured to an upper exterior portion of the flexible sheath by a first pair of hook and loop patches interposed therebetween, the upper web continuing into a connecting web extendable between the lateral sound tubes of a stethoscope and folding back into a parallel orientation with the upper web to terminate in a lower web, the lower web being of a substantially coextensive construction relative to the upper web and being removably coupled to a lower exterior surface of the flexible sheath in a diametrically opposed orientation relative to the coupling of the upper web to the flexible sheath by a second pair of hook and loop patches interposed between the lower web and the flexible sheath.

* * * * *